(12) United States Patent
Li et al.

(10) Patent No.: US 8,389,514 B2
(45) Date of Patent: *Mar. 5, 2013

(54) CYANOAMINOQUINOLONES AND TETRAZOLOAMINOQUINOLONES AS GSK-3 INHIBITORS

(75) Inventors: Bei Li, San Diego, CA (US); Anna Katrin Szardenings, Torrance, CA (US)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 165 days.

This patent is subject to a terminal disclaimer.

(21) Appl. No.: 12/677,789

(22) PCT Filed: Sep. 11, 2008

(86) PCT No.: PCT/US2008/010615
§ 371 (c)(1),
(2), (4) Date: Aug. 5, 2010

(87) PCT Pub. No.: WO2009/035634
PCT Pub. Date: Mar. 19, 2009

(65) Prior Publication Data
US 2011/0172219 A1   Jul. 14, 2011

Related U.S. Application Data

(60) Provisional application No. 60/993,346, filed on Sep. 11, 2007.

(51) Int. Cl.
C07D 498/06   (2006.01)
A61K 31/5383  (2006.01)
(52) U.S. Cl. .................................... 514/230.2; 544/101
(58) Field of Classification Search ................... 544/101; 514/230.2
See application file for complete search history.

(56) References Cited

U.S. PATENT DOCUMENTS

| | | | |
|---|---|---|---|
| 3,536,809 A | 8/1971 | Bennett et al. |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,328,245 A | 5/1982 | Yu et al. |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,762,832 A | 8/1988 | Grohe et al. |
| 4,847,375 A | 7/1989 | Grohe et al. |
| 4,990,508 A | 2/1991 | Narita et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,153,203 A | 10/1992 | Yatsunami et al. |
| 5,190,923 A | 3/1993 | Vincent et al. |
| 5,323,907 A | 6/1994 | Kalvelage |
| 5,354,556 A | 10/1994 | Sparks et al. |
| 5,387,748 A | 2/1995 | Demuth, Jr. et al. |
| 5,430,152 A | 7/1995 | Saukaitis et al. |
| 5,519,016 A | 5/1996 | Kimura et al. |
| 5,591,767 A | 1/1997 | Mohr et al. |
| 5,612,059 A | 3/1997 | Cardinal et al. |
| 5,638,480 A | 6/1997 | Bodmer et al. |
| 5,639,476 A | 6/1997 | Oshlack et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |

(Continued)

FOREIGN PATENT DOCUMENTS

CN   1181381        11/1997
EP   0265230 A1     4/1988

(Continued)

OTHER PUBLICATIONS

Chu, et al., J. Heterocyclic Chem., 24, 453, 1987.
Dax, et al., J. Org. Chem., 57, 744, 1992.
Hayakawa, et al., Chem. Pharm. Bull., 32, 4907, 1984.
Ishikawa et al., Chem. Pharm. Bull., 37, 2103, 1989.
Ishikawa et al., Chem. Pharm. Bull., 38, 2459, 1990.

(Continued)

*Primary Examiner* — Kahsay T Habte
(74) *Attorney, Agent, or Firm* — Jones Day

(57) ABSTRACT

Provided herein are aminoquinolones and pharmaceutically acceptable derivatives thereof. In certain embodiments, provided herein are compounds, compositions and methods for treating, preventing or ameliorating GSK-3 mediated diseases.

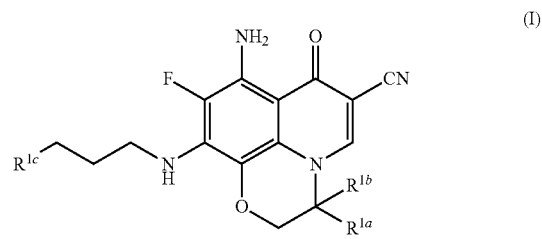

(I)

23 Claims, No Drawings

U.S. PATENT DOCUMENTS

| | | | |
|---|---|---|---|
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,221,633 B1 | 4/2001 | Ertl et al. |
| 6,221,897 B1 | 4/2001 | Frick et al. |
| 6,245,744 B1 | 6/2001 | Frick et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,342,512 B1 | 1/2002 | Kirsch et al. |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 6,825,353 B2 | 11/2004 | Saito et al. |
| 6,967,205 B1 | 11/2005 | Abdul-Rahman |
| 2004/0132764 A1 | 7/2004 | Locher |
| 2005/0054663 A1 | 3/2005 | Bennett et al. |
| 2005/0182085 A1 | 8/2005 | Defossa et al. |
| 2007/0254866 A1 | 11/2007 | Cociorva et al. |
| 2010/0234367 A1 | 9/2010 | Nomura et al. |
| 2011/0034436 A1 | 2/2011 | Cociorva et al. |

FOREIGN PATENT DOCUMENTS

| | | |
|---|---|---|
| EP | 0390215 A2 | 10/1990 |
| EP | 0462884 A1 | 6/1993 |
| EP | 0945435 A1 | 9/1999 |
| EP | 1486488 A1 | 12/2004 |
| EP | 1650192 A1 | 4/2006 |
| ES | 0206819 A6 | 5/1992 |
| JP | S591489 A | 1/1984 |
| JP | 62198685 A | 2/1986 |
| JP | S6253987 A | 5/1986 |
| JP | S62167769 A | 1/1987 |
| JP | S62252772 A | 4/1987 |
| JP | S63264439 A | 1/1988 |
| JP | S63132891 A | 6/1988 |
| JP | 03133983 A | 10/1989 |
| JP | H1268679 A | 10/1989 |
| JP | H525162 A | 2/1993 |
| WO | WO9726265 A1 | 7/1997 |
| WO | WO9741097 A2 | 11/1997 |
| WO | WO9808871 A1 | 3/1998 |
| WO | WO9903861 A1 | 1/1999 |
| WO | WO9915525 A1 | 4/1999 |
| WO | WO9965897 A1 | 12/1999 |
| WO | WO0038675 A1 | 7/2000 |
| WO | WO0040569 A1 | 7/2000 |
| WO | WO0063208 A1 | 10/2000 |
| WO | WO0066585 A1 | 11/2000 |
| WO | WO0071549 A1 | 11/2000 |
| WO | WO0078312 A1 | 12/2000 |
| WO | WO0109111 A1 | 2/2001 |
| WO | WO0183451 A1 | 11/2001 |
| WO | WO0185695 A1 | 11/2001 |
| WO | WO0191752 A1 | 12/2001 |
| WO | WO0209758 A2 | 2/2002 |
| WO | WO0217918 A2 | 3/2002 |
| WO | WO02092571 A1 | 11/2002 |
| WO | WO0204462 A1 | 8/2003 |
| WO | WO2004019932 A1 | 3/2004 |
| WO | WO2004089930 | 10/2004 |
| WO | WO2004096221 A2 | 11/2004 |
| WO | WO2005007111 A2 | 1/2005 |

OTHER PUBLICATIONS

Okada, et al., J. Heterocyclic Chem., 28, 1067, 1991.
Parikh et al., J. Heterocyclic Chem., 25, 1567, 1988.
Asakawa et al., Horm, Metab. Re. 33 (9): 544-558, 2001.
Augeri, et al., J. Heterocyclic Chem., 27, 1509, 1990.
Yoshida et al., Synlett, 2003, 2139.
Coghlan, et al., Chemistry & Biology 7(10):793-03, 2000.
Cohen, et al., Nature Reviews, Drug Discovery, vol. 3, No. 6, 479-487, 2004.
Haq, et al., J. Cell. Biol. 151(1):117-29, 2000.
Kim, et al., Curr. Opin. Genetics & Dev. 10:508-14, 2000.
Lee, et al., Drugs of the Future 26(9):873-81, 2001.
Salvador, et al., Expert Opinion on Pharmacotherapy 2(10):1615-22, 2001.
Santus and Baker, J. Controlled Release, 35, 1-21, 1995.
Verma, et al., Drug Development and Industrial Pharmacy, 26, 695-708, 2000.
Verma, et al., J. Controlled Release, 79, 7-27, 2002.
Atarashi, et al., Chem. Pharm. Bull. 35(5):1896-902, 1987.
Atarashi, et al., J. Heterocyclic Chem., 28, 329, 1991.
Buchwald, et al., Surgery 88(4):507-16, 1980.
Calas, et al., Eur. J. Med. Chem. 26:279-290, 1991.
Doyle, et al., J. Org. Chem. 42(14): 2426-31, 1977.
Egawa, et al., Chem. Pharm. Bull., 34, 4098,, 1986.
Fujita, et al., Chem. Pharm. Bull. 44(5):987-90, 1996.
Golub, et al., J. Med. Chem 49: 6443, 2006.
Todo et al., Chem. Pharm. Bull. 42(12) 2569-2574, 1994.
Havlicek, et. al., J. Med. Chem. 40:408-12, 1997.
Kaiho, et al., J. Med. Chem., 32, 351, 1989.
Kawatsura, et al., Tetrahedron, 63, 4172, 2007.
Kiely, et al., J. Heterocyclic Chem. 26(6):1675-81, 1989.
Kiely, et al., J. Med. Chem. 31:2004-2008, 1988.
Kobayashi, et al., Org. Lett., 7, 1319, 2005.
Kobayashi, et al., Org. Lett., 7, 183, 2005.
Koga, et al., J. Med. Chem., 23, 1358, 1980.
Kondo, et al., J. Med. Chem. 31:221-25, 1988.
Langer, Science 249(4976):1527-33, 1990.
Mitscher, et al., J. Med. Chem., 30, 2283, 1987.
Miyamoto, et al., J. Med. Chem. 33:1645-56, 1990.
Scholmerich et al., Der Internist, No. 4, 533-543, 2001.
Remuzon, et al., J. Med. Chem.,, 34, 29, 1991.
Saloutin, et al., J. Fluoerine Chem. 65:37-41, 1993.
Saudek, et al., N. Engl. J. Med. 321(9):574-79, 1989.
Sbardella, et al., Il Farmaco 59:463-71, 2004.
Sefton, CRC Crit. Rev. Biomed. Eng. 14(3):201-40, 1987.
Shibamori, et al., Chem. Pharm. Bull. 38(9):2390-96, 1990.
Singh, R., et al., Eur. J. Med. Chem., 33:697-03, 1998.
Wentland, et al., J. Med. Chem. 31:1694-1697, 1988.
Wentland, et al, Bioorg. Med. Chem Lett. 3 (8) 1711-1716, 1993.
U.S.P.T.O. non-Final Office Action dated Oct. 16, 2008 for U.S. Appl. No. 11/718,000, filed on Mar. 13, 2007.
U.S.P.T.O. Final Office Action dated May 14, 2009 for U.S. Appl. No. 11/718,000, filed on Mar. 13, 2007.
U.S.P.T.O. non-Final Office Action dated Dec. 9, 2009 for U.S. Appl. No. 11/718,000, filed on Mar. 13, 2007.
U.S.P.T.O. non-Final Office Action dated Jul. 7, 2010 for U.S. Appl. No. 11/718,000, filed on Mar. 13, 2007.
U.S.P.T.O. Notice of Allowance Jan. 24, 2011 for U.S. Appl. No. 11/718,000, filed on Jan. 13, 2007.
U.S.P.T.O. Supplemental Notice of Allowance Feb. 8, 2011 for U.S. Appl. No. 11/718,000, filed on Jan. 13, 2007.
U.S.P.T.O. Notice of Allowance Jul. 20, 2011 for U.S. Appl. No. 11/718,000, filed on Jan. 13, 2007.
U.S.P.T.O. non-Final Office Action dated Nov. 2, 2010 for U.S. Appl. No. 12/721,454, filed on Mar. 10, 2010.
U.S.P.T.O. Notice of Allowance Apr. 8, 2011 for U.S. Appl. No. 12/721,454, filed on Mar. 10, 2010.
U.S.P.T.O. Notice of Allowance Jul. 14, 2011 for U.S. Appl. No. 12/721,454, filed on Mar. 10, 2010.

CYANOAMINOQUINOLONES AND TETRAZOLOAMINOQUINOLONES AS GSK-3 INHIBITORS

PRIORITY CLAIM

This application is the national phase entry pursuant to 35 U.S.C. §371 of International Application No. PCT/US2008/010615, filed Sep. 11, 2008, which claims priority to U.S. provisional application Ser. No. 60/993,346 filed Sep. 11, 2007 to Li et al. The disclosures of the above referenced applications are incorporated by reference in their entireties.

FIELD

Compounds, compositions and methods for treating GSK-3 mediated diseases are provided. In one embodiment, the compounds provided herein are cyanoaminoquinolones that are GSK-3 inhibitors. In one embodiment, the compounds provided herein are tetrazoloaminoquinolones that are GSK-3 inhibitors.

BACKGROUND

Glycogen synthase kinase-3 (GSK-3) is a serine/threonine protein kinase having α and β isoforms that are each encoded by distinct genes (Coghlan et al., *Chemistry & Biology*, 7, 793-803 (2000); and Kim and Kimmel, *Curr. Opinion Genetics Dev.*, 10, 508-514 (2000)). GSK-3 has been implicated in various diseases including diabetes, Alzheimer's disease, CNS disorders such as manic depressive disorder and neurodegenerative diseases, and cardiomyocete hypertrophy (see, e.g., WO 99/65897; WO 00/38675; and Haq et al., *J. Cell Biol.* (2000) 151, 117). These diseases may be caused by, or may result in, the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPB α. These diverse targets implicate GSK-3 in many aspects of cellular metabolism, proliferation, differentiation and development.

Small molecule inhibitors of GSK-3 have recently been reported (WO 99/65897 (Chiron) and WO 00/38675 (SmithKline Beecham)), however, there is a continued need to find more effective therapeutic agents to treat GSK-3 mediated diseases.

SUMMARY

Provided herein are compounds that are GSK-3 inhibitors, pharmaceutical compositions containing the compounds and methods of use thereof. In one embodiment, the compounds are cyanoaminoquinolones and pharmaceutically acceptable derivatives thereof. In one embodiment, the compounds are tetrazoloaminoquinolones and pharmaceutically acceptable derivatives thereof. In certain embodiments, the compounds for use in the compositions and methods provided herein are cyanoaminoquinolones of Formula I:

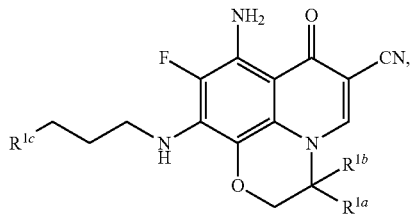

or a pharmaceutically acceptable derivative thereof, wherein the variables are chosen such that the resulting compounds show activity as GSK-3 inhibitors.

In certain embodiments, the compounds for use in the compositions and methods provided herein are tetrazoloaminoquinolones of Formula II:

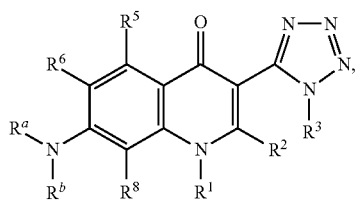

or a pharmaceutically acceptable derivative thereof, wherein the variables are chosen such that the resulting compounds show activity as GSK-3 inhibitors.

Pharmaceutical compositions containing a compound of Formula I or II and a pharmaceutically acceptable carrier are provided herein. Also provided are methods for treating, preventing, or ameliorating one or more symptoms of GSK-3 mediated diseases by administering the compounds and compositions provided herein.

In certain embodiments, provided herein are methods for inhibiting an action of GSK-3 by administering compounds and compositions provided herein. In other embodiments, provided herein are methods for treatment, prevention, or amelioration of one or more GSK-3-mediated diseases. In other embodiments, provided herein are methods for treatment, prevention, or amelioration of one or more symptoms of diseases or conditions including, but not limited to conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases such as acute stroke, epilepsy, mood disorders such as depression, schizophrenia and bipolar disorders, rheumatoid arthritis, inflammatory bowel disease, ulceractive colitis, Crohn's disease, sepsis, pancreatic cancer, ovarian cancer and osteoporosis by administering compounds and compositions provided herein.

DETAILED DESCRIPTION OF EMBODIMENTS

A. Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein "subject" is an animal, typically a mammal, including human, such as a patient.

The terms "GSK-3 mediated disease, or "GSK-3 mediated condition", as used herein, mean any disease or other deleterious condition or state in which GSK-3 is known to play a role. Such diseases or conditions include, without limitation, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases such as acute stroke, epilepsy, mood disorders such as depression, schizophrenia and bipolar disorders, rheumatoid arthritis, inflammatory bowel disease, ulceractive colitis, Crohn's disease, sepsis, pancreatic cancer, ovarian cancer and osteoporosis.

As used herein, biological activity refers to the in vivo activities of a compound or physiological responses that result upon in vivo administration of a compound, composition or other mixture. Biological activity, thus, encompasses therapeutic effects and pharmacokinetic behaviour of such compounds, compositions and mixtures. Biological activities can be observed in in vitro systems designed to test for such activities.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C (OR) where R is hydrogen, alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating diabetes.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the $IC_{50}$ refers to an amount, concentration or dosage of a particular test compound that achieves a 50% inhibition of a maximal response in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the term GSK3 inhibitor refers to a compound that exhibits an $IC_{50}$ with respect to GSK3 of no more than about 100 µM, and in one embodiment, no more than about 50 µM, as measured in the cell-free assay for GSK3 inhibitory activity described generally hereinbelow. In certain embodiments, compounds provided herein exhibit an $IC_{50}$ with respect to GSK3 of no more than about 10 µM, in one embodiment, no more than about 5 µM, or no more than 1 µM, as measured in the cell-free GSK3 kinase assay.

As used herein, the term selective refers to a relatively greater potency for inhibition against GSK3, as compared to at least one other type of kinase, such as CDK5 kinase. In certain embodiments, GSK3 inhibitor compounds provided herein are selective with respect to GSK3, as compared to at least two other types of kinases, such as CDK5 and CDK2 kinase. Kinase activity assays for kinases other than GSK3 are described herein and are generally known. See e.g., Havlicek et. al., *J. Med. Chem.*, 40: 408-12 (1997), incorporated herein by reference. An inhibitor that is selective for GSK3 exhibits a GSK3 selectivity of greater than about 1-fold, 2-fold, 5-fold, 10 fold, 20-fold, 50-fold or greater than about 100-fold with respect to inhibition of a kinase other than GSK3. As used herein, the term "other kinase" refers to a kinase other than GSK3. Such selectivities are generally measured in cell-free assays.

As used herein, substantially free of antibacterial activity or having very low antibacterial activity means the antibacterial activity measured, as a minimum inhibitory concentration (MIC), for a test compound is greater than about 0.5 µM, 1 µM, 5 µM, 10 µM, 50 µM, 75 µM, 100 µM, 150 µM, 200 µM or 250 µM. In some embodiments, MIC is with respect to inhibition of growth of *E. Coli* and/or *S. aureus*.

As used herein, a minimum inhibitory concentration (MIC) for bacterial growth assay is the lowest level of a compound needed to cause an inhibition to bacterial growth in culture medium. In certain embodiments, the antibacterial activity of compounds herein, measured as MIC.

As used herein, bioavailability refers to the rate and extent of absorption of the test compound. Methods for determining bioavailability are well known to those of skill in the art. For example, bioavailability of any of the compounds described herein can be determined empirically by administration of the compound to an animal, followed by taking blood samples over time and measuring the blood concentration of the compound. In vivo half life (t½) is defined as the time it takes for the concentration of the compound in the blood to be reduced by one-half. Estimations of the area under the curve for intravenous administration can be used to estimate the area under the curve for oral administration, yielding bioavailability data. See, e.g., Milo Gibal (1991) *Biopharmaceutics and Pharmacology,* 4th edition (Lea and Sediger).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures.

As used herein, substantially pure means sufficiently homogeneous to appear free of readily detectable impurities as determined by standard methods of analysis, such as thin layer chromatography (TLC), gel electrophoresis, high performance liquid chromatography (HPLC), nuclear magnetic resonance (NMR), and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, 1 to 16 carbons or 1 to 6 carbons and are straight or branched. In certain embodiments, alkyl, alkenyl and alkynyl carbon chains contain from 1 to 6 carbons. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. The alkenyl carbon chains of 2 to 6 carbons, in certain embodiments, contain 1 to 2 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Alkynyl carbon chains of from 2 to 6 carbons, in certain embodiments, contain 1 to 2 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, vinyl, 1-propenyl, 2-propenyl, isopropenyl, 1-butenyl, 2-butenyl, 3-butenyl, 1,3-butadienyl, ethynyl, 1-propynyl and 2-propynyl. As used herein, lower alkyl, lower alkenyl, and lower alkynyl refer to carbon chains having from 1 or 2 carbons up to about 6 carbons.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, generally selected from $Q^0$ or $Q^1$.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is (are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, aminocarbonyl, alkoxycarbonyl, guanidino, or the nitrogen may be quaternized to form an ammonium group where the substituents are selected as above.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, generally selected from $Q^0$ or $Q^1$.

As used herein, "aralkyl" refers to an alkyl group in which one of the hydrogen atoms of the alkyl is replaced by an aryl.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. "Lower haroalkyl" refers to a lower alkyl group in which one or more of the hydrogen atoms are replaced by halogen. Such groups include, but are not limited to, chloromethyl, trifluoromethyl and 1-chloro-2-fluoroethyl.

As used herein, "fused heterocyclylaryl" refers to fused heterocyclyl and aryl. In one embodiment, fused heterocyclylaryls are those wherein heterocyclyl contains about 5 to about 6 ring atoms and the aryl thereof is phenyl. A fused heterocyclylaryl may be bonded through any atom of the ring system. Representative fused heterocyclylaryl groups include 1,3-benzodioxolan-4-yl, 1,3-benzodioxolan-5-yl, 1,3-benzodioxolan-6-yl, 1,3-benzodioxolan-7-yl, 4-indolinyl, 5-indolinyl, 6-indolinyl and 7-indolinyl.

As used herein, "fused arylheterocyclyl" refers to fused aryl and heterocyclyl. In one embodiment, fused arylheterocyclyls are those wherein the aryl thereof is phenyl and the heterocyclyl contains about 5 to about 6 ring atoms. A fused arylheterocyclyl may be bonded through any atom of the ring system. Representative fused arylheterocyclyl groups include 1-indolinyl, 2-indolinyl, 3-indolinyl, 1,2,3,4-tetrahydroqunolin-1-yl, 1,2,3,4-tetrahydroqunolin-2-yl, 1,2,3,4-tetrahydroqunolin-3-yl and 1,2,3,4-tetrahydroqunolin-4-yl.

As used herein, "haloalkoxy" refers to RO— in which R is a haloalkyl group.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "arylalkylaminocarbonyl" refers to —C(O)NRR' in which one of R and R' is aryl, such as phenyl, and the other of R and R' is alkyl, including lower alkyl.

As used herein, "arylaminocarbonyl" refers to —C(O)NHR in which R is aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, such as phenyl.

Where the number of any given substituent is not specified (e.g., "haloalkyl"), there may be one or more substituents present. For example, "haloalkyl" may include one or more of the same or different halogens. "C$_{1-3}$alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

Provided herein are GSK3 inhibitor compounds, compositions containing the compounds and methods of use thereof. In certain embodiments, compounds provided herein exhibit an IC$_{50}$ with respect to GSK3 of no more than about 1 µM or no more than about 0.5 µM, as measured in the cell-free GSK3 kinase assay. In certain embodiments, compounds provided herein exhibit inhibitory activity that is selective with respect to GSK3, as compared to at least one other type of kinase. In certain embodiments, GSK3 inhibitors provided herein exhibit a selectivity for GSK3, as compared to at least one other kinase, of at least about 1 fold, 2-fold, 5-fold, 10-fold, or at least about 100-fold, or at least about 1000-fold.

In certain embodiments, GSK3 inhibitors provided herein are substantially free of antibacterial activity or having very low antibacterial activity. The antibacterial activity can be measured by methods known in the art by estimating a minimum inhibitory concentration (MIC) for test compounds. A MIC is the lowest level of a compound needed to cause an inhibition to bacterial growth in a culture medium. In certain embodiments, the antibacterial activity of compounds herein, measured as a minimum inhibitory concentration with respect to inhibition of growth of *E. Coli* and/or *S. aureus* is greater than about 10 µM, 50 µM, 75 µM, 100 µM, 150 µM, 200 µM or 250 µM. (Clinical and Laboratory Standards Institute. Methods for Dilution Antimicrobial Susceptibility Tests for Bacteria That Grow Aerobically; Approved Standard-Sixth Edition: CLSI document M7-A4. CLSI, Wayne, Pa. (2003))

In certain embodiments, the compounds provided herein have enhanced tolerability as compared to similar compounds known in the art. Such enhanced tolerability is manifested through alteration of the pharmacokinetic profile of the compounds. The pharmacokinetic profile is based on a number of factors, including, but not limited to, bioavailability, in vivo half-life and in vivo efficacy. In certain embodiments, the compounds provided herein have improved properties including but not limited to potency, stability and receptor-selectivity as compared to similar compounds known in the art.

I. Compounds of Formula I

In certain embodiments, the compounds for use in the compositions and methods provided herein are of Formula I:

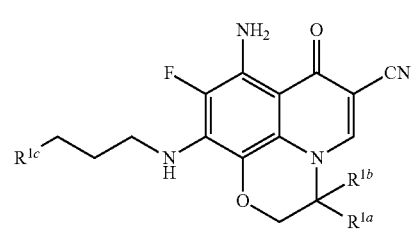

or pharmaceutically acceptable derivatives thereof, wherein

R$^{1a}$ and R$^{1b}$ are each independently hydrogen or lower alkyl, and R$^{1c}$ is a substituted or unsubstituted pyridinyl; wherein the substituents when present are selected from one or more lower alkyl groups, with a proviso that a) when one of $R^{1a}$ and $R^{1b}$ is hydrogen and the other is methyl, and b) $R^{1c}$ is pyridin-2-yl, then $R^{1c}$ is substituted with one or more lower alkyl groups.

In certain embodiments, the compounds for use in the compositions and methods provided herein have Formula I, wherein $R^{1a}$ and $R^{1b}$ are each lower alkyl. In certain embodiments, $R^{1a}$ and $R^{1b}$ are each methyl. In certain embodiments, $R^{1a}$ and $R^{1b}$ are each hydrogen.

In certain embodiments, $R^{1a}$ is hydrogen and $R^{1b}$ is lower alkyl. In certain embodiments, $R^{1a}$ is hydrogen and $R^{1b}$ is methyl.

In certain embodiments, $R^{1c}$ is substituted with one or more lower alkyl groups. In certain embodiments, $R^{1c}$ is substituted with one or more methyl groups.

In certain embodiments, the compound is of Formula:

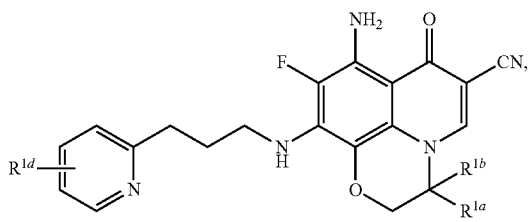

or a pharmaceutically acceptable derivative thereof, wherein $R^{1d}$ is hydrogen or lower alkyl and the other variables are as described elsewhere herein. In one embodiment, $R^{1d}$ is hydrogen or methyl. In one embodiment, $R^{1d}$ is hydrogen. In one embodiment, $R^{1d}$ is methyl.

In certain embodiments, the compound is of Formula:

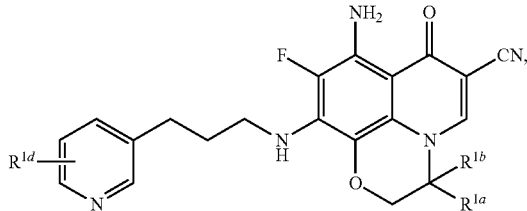

or a pharmaceutically acceptable derivative thereof, wherein the variables are as described elsewhere herein.

In certain embodiments, the compound is of Formula:

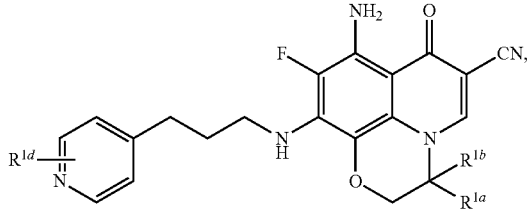

or a pharmaceutically acceptable derivative thereof, wherein the variables are as described elsewhere herein.

In certain embodiments, the compound is of Formula:

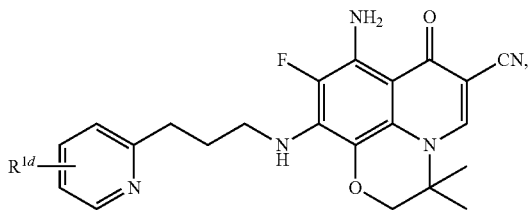

or a pharmaceutically acceptable derivative thereof, wherein the variables are as described elsewhere herein.

In certain embodiments, the compound is of Formula:

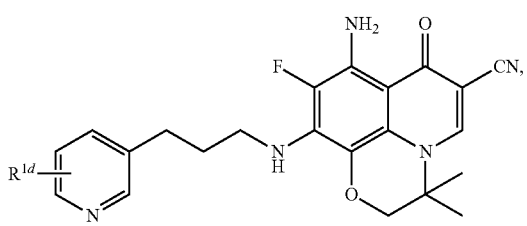

or a pharmaceutically acceptable derivative thereof, wherein the variables are as described elsewhere herein.

In certain embodiments, the compound is of Formula:

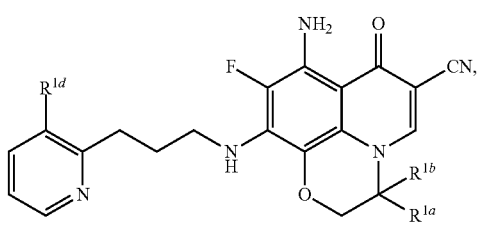

or a pharmaceutically acceptable derivative thereof, wherein the variables are as described elsewhere herein.

In certain embodiments, the compound is of Formula:

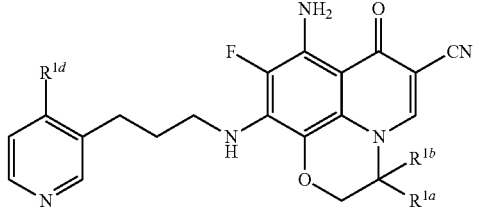

or a pharmaceutically acceptable derivative thereof, wherein the variables are as described elsewhere herein.

In certain embodiments, the compound is of Formula:

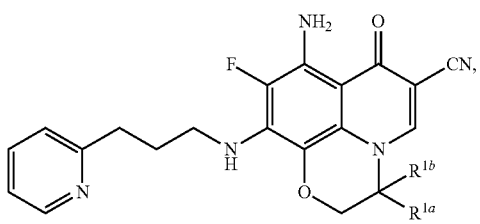

or a pharmaceutically acceptable derivative thereof, wherein the variables are as described elsewhere herein.

In certain embodiments, the compound is of Formula:

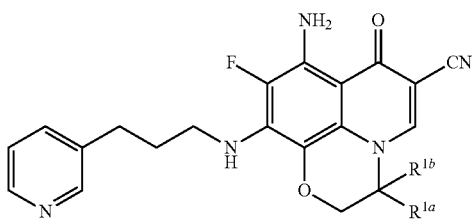

or a pharmaceutically acceptable derivative thereof, wherein the variables are as described elsewhere herein.

In certain embodiments, the compound is of Formula:

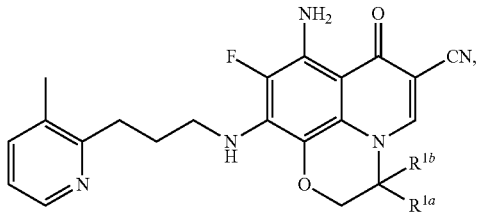

or a pharmaceutically acceptable derivative thereof, wherein the variables are as described elsewhere herein.

In certain embodiments, the compound is of Formula:

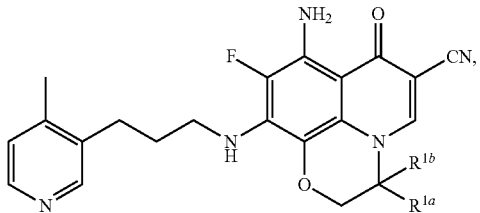

or a pharmaceutically acceptable derivative thereof, wherein the variables are as described elsewhere herein.

In certain embodiments, the compound is selected from

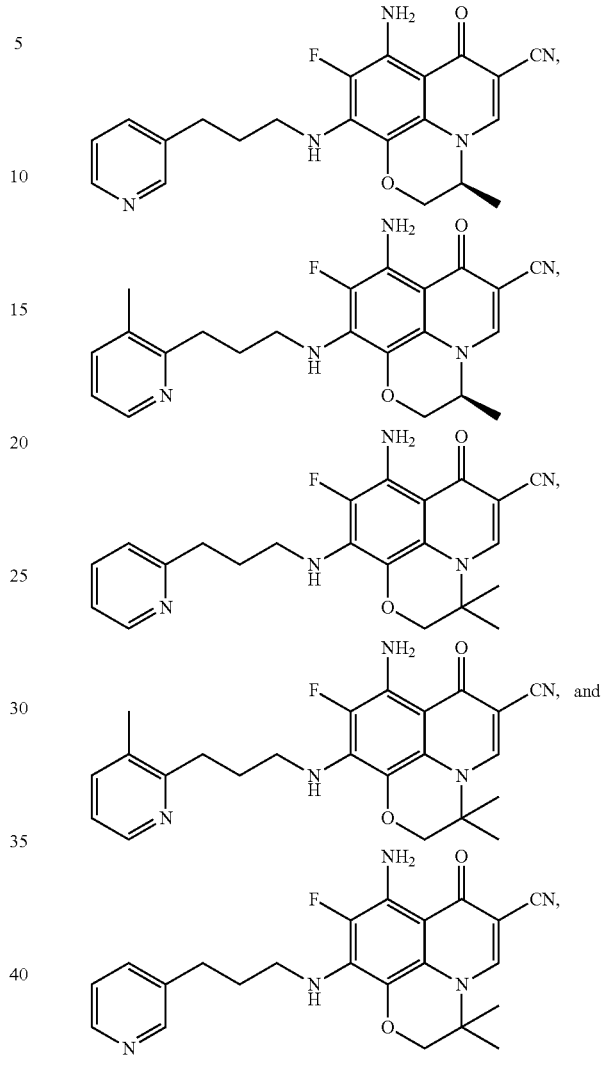

or a pharmaceutically acceptable derivative or salt thereof.

In certain embodiments, the compounds provided herein have improved properties over the compounds previously disclosed. Such properties include one or more of the following: activity, selectivity, pharmacokinetic properties, toxicity, bioavailability and others.

II. Compounds of Formula II

In certain embodiments, the compounds for use in the compositions and methods provided herein are tetrazoloquinolones of Formula II:

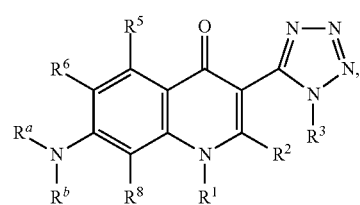

or pharmaceutically acceptable derivatives thereof, wherein $R^1$ and $R^8$ are as follows:

i) $R^1$ is hydrogen, lower alkyl, cycloalkyl, heterocyclyl, aryl, aralkyl, heterocycloalkyl or heteroaralkyl; and $R^8$ is hydrogen, halo or alkoxy; or ii) $R^1$ and $R^8$ together with the atoms on which they are substituted form a 5-8 membered substituted or unsubstituted heterocyclic or heteroaryl ring containing 1-4 heteroatoms; wherein the substituents when present are selected from one or more $Q^0$;

$Q^0$ is halo, hydroxyl, alkoxy, cycloalkyl, aryl, heteroaryl, aralkyl, pseudohalo, amino, nitro, alkyl, haloalkyl, alkenyl or alkynyl;

$R^2$ is hydrogen, lower alkyl, $COOR^{2a}$ or optionally substituted aryl, wherein the substituents when present are selected from one to four $Q^1$ groups;

$R^{2a}$ is hydrogen, or lower alkyl;

$R^3$ is H or lower alkyl;

$R^5$ is $NR^{5a}R^{5b}$ or $SR^{5a}$;

$R^{5a}$ and $R^{5b}$ are each independently hydrogen, lower alkyl or $COR^{5C}$;

$R^{5C}$ is lower alkyl or lower haloalkyl;

$R^6$ is halo;

$R^a$ and $R^b$ are selected as follows:

i) $R^a$ is hydrogen or lower alkyl, and $R^b$ is
—$(CH_2)_n(NR^c)_mR$,
—$(CH_2)_nOR^d$,
—$(CH_2)_nS(O)_lR^d$,
—$CH(R^j)(CH_2)_n(NR^c)_mR$
—$CH(R^j)(CH_2)_nOR^d$, or
—$CH(R^j)(CH_2)_nS(O)_lR^d$ ii) $R^a$ and $R^b$ together with the nitrogen atom on which they are substituted form a 5-7 membered substituted or unsubstituted heterocyclic or heteroaryl ring containing 1-4 heteroatoms; wherein the substituents when present are selected from one to four $Q^1$ groups;

$R^c$ is hydrogen or lower alkyl;

R is alkyl, aryl, heteroaryl, cycloalkyl, heterocyclyl, fused heterocyclylaryl, fused arylheterocyclyl, —$C(O)OR^d$, —$C(O)R^dC(O)NR^eR^e$ or —$CHR^dR^d$;

each $R^d$ is alkyl, aryl, heterocyclyl, heteroaryl, cycloalkyl, fused heterocyclylaryl or fused arylheterocyclyl;

each $R^e$ is hydrogen, alkyl, aryl, heterocyclyl, heteroaryl, cycloalkyl, fused heterocyclylaryl or fused arylheterocyclyl;

$R^j$ is lower alkyl or lower haloalkyl;

n is 0 to 6;

m is 0 or 1; and l is 0 to 2, where R and $R^d$ are optionally substituted with 1 to 4 substituents, each independently selected from $Q^1$, where $Q^1$ is as defined elsewhere herein.

In certain embodiments, $R^1$, $R^2$, $R^b$, R and $R^d$ are optionally substituted with one or more, in certain embodiments, 1, 2, 3 or 4 substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroary-loxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(\!=\!O)(R^{50})_2$, $OP(\!=\!O)(R^{50})_2$, —$NR^{60}C(\!=\!O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., —O—$(CH_2)_y$—O—), thioalkylenoxy (i.e., —S—$(CH_2)_y$—O—) or alkylenedithioxy (i.e., —S—$(CH_2)_y$—S—) where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q$^2$ groups, which substitute atoms in a 1, 2 or 1,3 arrangement, together form alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two Q$^2$ groups, which substitute the same atom, together form alkylene;

R$^{50}$ is hydroxy, alkoxy, aralkoxy, alkyl, heteroaryl, heterocyclyl, aryl or —NR$^{70}$R$^{71}$, where R$^{70}$ and R$^{71}$ are each independently hydrogen, alkyl, aralkyl, aryl, heteroaryl, heteroaralkyl or heterocyclyl, or R$^{70}$ and R$^{71}$ together form alkylene, azaalkylene, oxaalkylene or thiaalkylene;

R$^{51}$, R$^{52}$ and R$^{53}$ are each independently hydrogen, alkyl, aryl, aralkyl, heteroaryl, heteroaralkyl, heterocyclyl or heterocyclylalkyl;

R$^{60}$ is hydrogen, alkyl, aryl, aralkyl, heteroaryl, heteroaralkyl, heterocyclyl or heterocyclylalkyl; and R$^{63}$ is alkoxy, aralkoxy, alkyl, heteroaryl, heterocyclyl, aryl or —NR$^{70}$R$^{71}$.

In certain embodiments, compounds provided herein are selected with a proviso that if m=1, R is not alkyl or cycloalkyl.

In certain embodiments, R and R$^d$ are optionally substituted with one, two, three or four Q$^1$ substituents.

In certain embodiments, n is 1-6.

In certain embodiments, the compound is of Formula IIA:

or pharmaceutically acceptable derivatives thereof, wherein R$^x$ and R$^y$ are each independently hydrogen or lower alkyl and the other variables are as described elsewhere herein. In one embodiment, the compound has formula IIA, wherein R$^x$ and R$^y$ are each independently hydrogen or lower alkyl;

R$^a$ is hydrogen or lower alkyl;

R$^b$ is —(CH$_2$)$_n$(NR$^c$)$_m$R;

R$^c$ is hydrogen or lower alkyl;

R is aryl, heteroaryl or heterocyclyl;

n is 1-3; and m is 0 or 1.

In certain embodiments, the compound is of Formula:

or pharmaceutically acceptable derivatives thereof, wherein R$^b$ and the other variables are as described elsewhere herein.

In certain embodiments, the compound is of Formula:

or pharmaceutically acceptable derivatives thereof, wherein the variables are as described elsewhere herein.

In certain embodiments, the compound is of Formula:

or pharmaceutically acceptable derivatives thereof, wherein the variables are as described elsewhere herein.

In certain embodiments, the compound is of Formula:

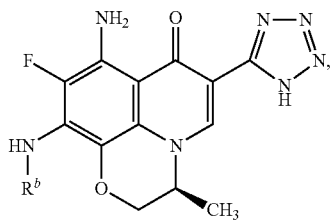

or pharmaceutically acceptable derivatives thereof, wherein the variables are as described elsewhere herein.

In certain embodiments, the compound is of Formula:

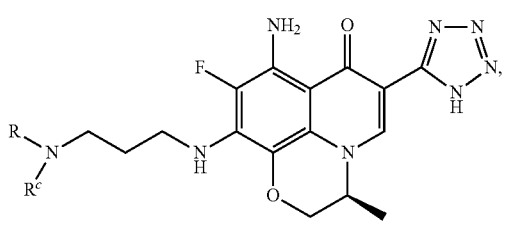

or pharmaceutically acceptable derivatives thereof, wherein R is aryl and $R^c$ is hydrogen or lower alkyl. In one embodiment, $R^c$ is lower alkyl. In one embodiment, $R^c$ is methyl or ethyl. In one embodiment, R is phenyl.

In certain embodiments, the compound is of Formula:

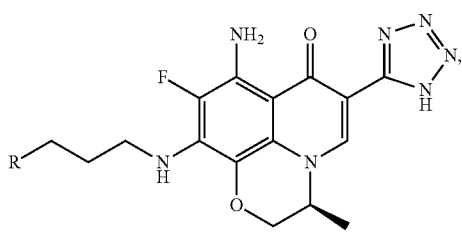

or pharmaceutically acceptable derivatives thereof, wherein R is 5 or 6 membered heteroaryl or heterocyclyl. In one embodiment, R is 5 or 6 membered heteroaryl. In one embodiment, R is pyridyl or imidazolyl.

In certain embodiments, the compound is selected from:

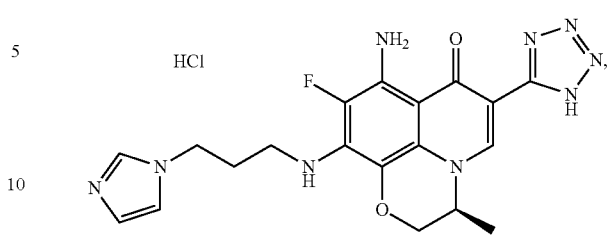

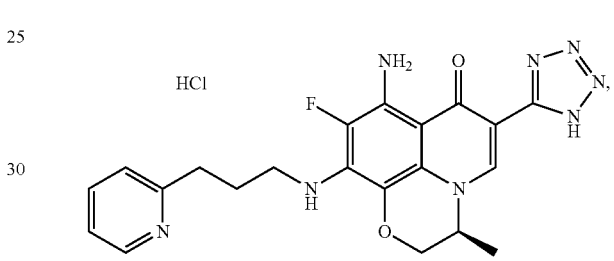

or a pharmaceutically acceptable derivative or salt thereof.

In certain embodiments, the compound is a pharmaceutically acceptable salt of the compounds provided herein. In one embodiment, the pharmaceutically acceptable salt is a hydrochloride salt.

For exemplary compounds, $IC_{50}$ (μM) for GSK3β enzyme in cell free assay is provided in Table 1 as follows: A<0.01 μM and B=0.01-0.1 μM.

Antibacterial activity for *E. coli*, ATCC8739 and *S. aures* Smith is expressed as MIC (μM).

TABLE 1

| Structure | GSK3β IC50 (μM) | Antibacterial Activity | |
|---|---|---|---|
| | | *E. Coli* | *S. aureus* Smith |
| 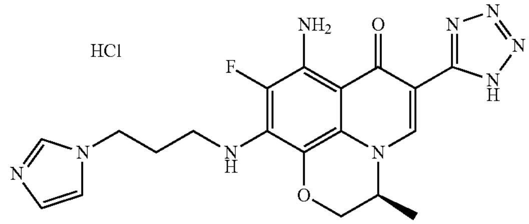 [SMILES: C[C@H]1COc2c(NCCCn3ccnc3)c(F)c(N)c3c(=O)c(-c4nnn[nH]4)cn1c23 ; Cl] | B | >257 | >257 |

TABLE 1-continued

| Structure | GSK3β IC50 (µM) | Antibacterial Activity | |
|---|---|---|---|
| | | E. Coli | S. aureus Smith |
| [structure with NH2, F, phenyl-N(ethyl)-propyl-NH-, tetrazole] | B | NA | NA |
| HCl · [structure with NH2, F, pyridin-2-yl-propyl-NH-, tetrazole] | A | NA | NA |

Preparation of the Compounds

The compounds provided herein can be prepared by methods known to one of skill in the art by routine modification of one or more methods known in the art by substituting appropriate readily available reagents (for example, see, International Patent Application No. PCT/US07/06480) and as exemplified in the Examples herein. Salts, acids and other derivatives thereof can be synthesized by methods known to those of skill in the art.

For the chiral compounds, the R- and S-isomers may be prepared according to any techniques known to those of skill in the art. For instance, they may be prepared by chiral or asymmetric synthesis from a suitable optically pure precursor or obtained from a racemic mixture by any conventional technique, for example, by chromatographic resolution using a 'chiral' column, TLC or by the preparation of diastereoisomers, separation thereof and regeneration of the desired isomer. See, e.g., "Compounds, Racemates and Resolutions," by J. Jacques, A. Collet, and S. H. Wilen, (Wiley-Interscience, New York, 1981); *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

D. Formulation of Pharmaceutical Compositions

The pharmaceutical compositions provided herein contain therapeutically effective amounts of one or more of compounds provided herein that are useful in the prevention, treatment, or amelioration of one or more of the symptoms of GSK-3 mediated diseases.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of GSK-3 mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of GSK-3 mediated diseases.

Typically a therapeutically effective dosage should produce a serum concentration of active ingredient of from about 0.1 ng/ml to about 50-100 μg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 mg to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing GSK-3 mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect; in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as GSK-3 mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative.

An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984). In some embodiments, a controlled release device is introduced into a subject in proximity of the site of inappropriate immune activation or a tumor. Other controlled release systems are discussed in the review by Langer (*Science* 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

8. Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of one or more symptoms associated with GSK-3 activity, and a label that indicates that the compound or pharmaceutically acceptable derivative thereof is used for treatment, prevention or amelioration of one or more symptoms of GSK-3 mediated diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

E. Evaluation of the Activity of the Compounds

Standard physiological, pharmacological and biochemical procedures are available for testing the compounds to identify those that possess a desired biological activity. GSK3 inhibitory activity of the compounds provided herein can be readily detected using the assays described herein, as well as assays generally known to those of ordinary skill in the art.

Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function either by direct interaction with GSK3 itself, or by interference with GSK3 expression or with post-translational processing required to produce mature active GSK3. U.S. Application No. 20050054663 describes exemplary cell-free and cell-based GSK3 kinase assays. Exemplary assays used herein are discussed briefly below:

Luciferase-Coupled Protein Kinase Assays

All coupled-luciferase assays are performed by using a brief incubation with firefly luciferase (Promega) after completion of the kinase assay. KinaseGlo Plus is used for reading kinase reactions with ATP>10 µM, KinaseGlo for ATP<10 µM. The assay volume in a 384-well plate for the kinase reaction is 30 microliters.

GSK3β

10-25 ng of recombinant full-length human GSK3β (Upstate) is incubated in the presence or absence of compound at varying concentrations for 1 hour at 30 degrees Celsius in 20 mM MOPS, pH 7.0, 10 mM magnesium acetate, 0.2 mM EDTA, 2 mM EGTA, 30 mM magnesium chloride, 62.5 µM phospho-glycogen synthase peptide-2, 5 µM ATP, 10 mM β-glycerol phosphate, 1 mM sodium orthovanadate and 1 mM dithiothreitol. Proceed to KinaseGlo luciferase reaction (see below).

CDK2

20-50 ng of recombinant full-length human CDK2 (Upstate) complexed with recombinant, human full length Cyclin A (Upstate) is incubated in the presence or absence of compound at varying concentrations for 1 hour at 30 degrees Celsius in 20 mM MOPS, pH 7.0, 0.2 mM EDTA, 2 mM EGTA, 30 mM magnesium chloride, 1 mg/mL Histone HI (Roche), 10 µM ATP, 10 mM β-glycerol phosphate, 1 mM sodium orthovanadate and 1 mM dithiothreitol. Proceed to KinaseGlo Plus luciferase reaction (see below).

CDK5

10-25 ng of recombinant full-length human CDK5 complexed with recombinant, human full length p35 (Upstate), is incubated in the presence or absence of compound at varying concentrations for 1 hour at 30 degrees Celsius in 20 mM MOPS, pH 7.0, 0.2 mM EDTA, 2 mM EGTA, 30 mM magnesium chloride, 1 mg/mL Histone HI (Roche), 10 µM ATP, 10 mM n-glycerol phosphate, 1 mM sodium orthovanadate and 1 mM dithiothreitol. Proceed to KinaseGlo Plus luciferase reaction (see below).

Luciferase Reaction:

Following the completion of the kinase reaction an equal volume of KinaseGlo or KinaseGlo Plus luciferase reagent (Promega) is added and the luminescence read using a luminescence plate reader within 5-10 minutes. Compound activity is expressed as % inhibition relative to maximal inhibition observed at the maximal dose and IC50 values then calculated using curve fitting software (GraphPad Prizm).

F. Methods of Use of the Compounds and Compositions

Methods of use of the compounds and compositions are also provided. The methods involve both in vitro and in vivo uses of the compounds and compositions.

In certain embodiments, provided herein are methods for inhibiting an action of GSK-3 by administering a compound provided herein or a pharmaceutically acceptable derivative thereof. In certain embodiments, provided herein are methods for treatment, prevention or amelioration of a GSK-3 mediated disease, including but not limited to diabetes, conditions associated with diabetes, Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases, depression, bipolar mood disorders, rheumatoid arthritis, inflammatory bowel disease, ulceractive colitis, Crohn's disease, sepsis, pancreatic cancer, ovarian cancer and osteoporosis. In one embodiment, the GSK-3 mediated disease is diabetes.

G. Combination Therapy

The compounds provided herein may be administered as the sole active ingredient or in combination with other active ingredients. Other active ingredients that may be used in combination with the compounds provided herein include but are not limited to, compounds known to treat GSK-3 mediated diseases such as conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders. Administration of the active ingredient combination may take place either by separate administration of the active ingredients to the patient or in the form of combination products in which a plurality of active ingredients are present in one pharmaceutical preparation.

In certain embodiments, the compound provided herein can be administered in combination with one or more GSK-3 inhibitor compounds known in the art. Such compounds are described in, for example, International Application No. PCT/US07/06480 and International Publication Nos. WO 99/65897 and WO 00/38675.

In certain embodiments, the compound provided herein can be administered in combination with one or more antidiabetics known in the art. The antidiabetics include insulin and insulin derivatives such as, for example, Lantus® (see www-.lantus.com) or HMR 1964, fast-acting insulins (see U.S. Pat. No. 6,221,633), GLP-1 derivatives such as, for example, those disclosed in WO 98/08871 and orally effective hypoglycemic active ingredients.

The orally effective hypoglycemic active ingredients include, but are not limited to, sulfonylureas (e.g. tolbutamide, glibenclamide, glipizide or glimepiride), biguanidines (e.g. metformin), meglitinides (for example, repaglinide), oxadiazolidinediones, thiazolidinediones (for example, troglitazone, ciglitazone, pioglitazone, rosiglitazone or the compounds disclosed in WO 97/41097), glucosidase inhibitors (for example, miglitol or acarbose), glucagon antagonists, GLP-1 agonists, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment, the compounds provided herein can be administered in combination with an HMGCoA reductase inhibitor such as simvastatin, fluvastatin, pravastatin, lovastatin, atorvastatin, cerivastatin, rosuvastatin. In one embodiment, the compounds provided herein can be administered in combination with a cholesterol absorption inhibitor such as, for example, ezetimibe, tiqueside, pamaqueside. In one embodiment, the compounds provided herein can be administered in combination with a PPAR gamma agonist, such as, for example, rosiglitazone, pioglitazone, JTT-501, GI 262570. In one embodiment, the compounds provided herein can be administered in combination with PPAR alpha agonist, such as, for example, GW 9578, GW 7647. In one embodiment, the compounds provided herein can be administered in combination with a mixed PPAR alpha/gamma agonist. In one embodiment, the compounds of the Formula I or II are administered in combination with a fibrate such as, for example, fenofibrate, clofibrate, bezafibrate. In one embodiment, the compounds provided herein can be administered in combination with an MTP inhibitor such as, for example, implitapide, BMS-201038, R-103757. In another embodiment, the compounds provided herein can be administered in combination with bile acid absorption inhibitor (see, for example, U.S. Pat. No. 6,245,744 or U.S. Pat. No. 6,221,897), such as, for example, HMR 1741; a CETP inhibitor, such as, for example, JTF-705; a polymeric bile acid adsorbent such as, for example, cholestyramine, colesevelam; an LDL receptor inducer (see U.S. Pat. No. 6,342,512), such as, for example, HMR1171, HMR1586; an ACAT inhibitor, such as, for example, avasimibe; an antioxidant, such as, for example, OPC-14117; a lipoprotein lipase inhibitor, such as, for example, NO-1886; an ATP-citrate lyase inhibitor, such as, for example, SB-204990; a squalene synthetase inhibitor, such as, for example, BMS-188494; a lipoprotein(a) antagonist, such as, for example, CI-1027 or nicotinic acid; a lipase inhibitor, such as, for example, orlistat. In one embodiment, the compounds provided herein, such as compounds of Formula I or II are administered in combination with insulin.

In a further embodiment, the compounds provided herein, such as compounds of Formula I or II can be administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-((4-aminoquinazolin-2-ylamino)methyl)cyclo-hexylmethyl}amide; hydrochloride (CGP 71683A)), $MC_4$ agonists (e.g. 1-amino-1,2,3,4-tetrahydronaphthalene-2-carboxylic acid (2-(3a-benzyl-2-methyl-3-oxo-2,3,3a,4,6,7-hexahydropyrazolo(4,3-c)pyridin- -5-yl)-1-(4-chlorophenyl)-2-oxoethyl)-amide; (WO 01/91752)), orexin antagonists (e.g. 1-(2-methylbenzoxazol-6-yl)-3-(1,5)naphthyridin-4-ylurea; hydrochloride (SB-334867-A)), H3 agonists (3-cyclohexyl-1-(4,4-dimethyl- -1,4,6,7-tetrahydroimidazo(4,5-c)-pyridin-5-yl)propan-1-one oxalic acid salt (WO 00/63208)); TNF agonists, CRF antagonists (e.g. (2-methyl-9-(2,4,6-trimethylphenyl)-9H-1,3,9-triazafluoren-4-yl) dipropyla-mine (WO 00/66585)), CRF BP antagonists (e.g. urocortin), urocortin agonists, I33 agonists (e.g. 1-(4-chloro-3-methanesulfonylmethylpheny-1)-2-(2-(2,3-dimethyl-1H-indol-6-yloxy)-ethylamino)-ethanol hydrochloride (WO 01/83451)), MSH (melanocyte-stimulating hormone) agonists, CCK-A agonists (e.g. {2-(4-(4-chloro-2,5-dimethoxyphenyl)-5-(2-cyclohexyl-ethyl-)thiazol-2-ylcarbamoyl)-5, 7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1-H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622. In one embodiment, the other active ingredient is dexamphatamine or amphetamine. In one embodiment, the other active ingredient is fenfluramine or dexfenfluramine. In another embodiment, the other active ingredient is sibutramine. In one embodiment, the other active ingredient is orlistat. In one embodiment, the other active ingredient is mazindol or phentermine.

It will be appreciated that every suitable combination of the compounds provided herein with one or more of the aforementioned compounds and optionally one or more further pharmacologically active substances is contemplated herein.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof U.S. patents and publications referenced herein are incorporated by reference.

EXAMPLES

Example 1

Preparation of (S)-8-amino-9-fluoro-3-methyl-7-oxo-10-(3-(pyridin-3-yl)propylamino)-3,7-dihydro-2H-(1,4)oxazino(2,3,4-ij)quinoline-6-carbonitrile (S)-9,10-difluoro-3-methyl-8-nitro-7-oxo-3,7-dihydro-2H-(1,4)oxazino(2,3,4-ij)quinoline-6-carboxylic acid (2)

A solution of commercially available 1 (5 g, 17.8 mmol) in concentrated $H_2SO_4$ (25 ml) was treated portionwise at 0° C. with solid $KNO_3$ (3.7 g, 35.6 mmol). The mixture was then allowed to warm to room temperature. After stirring for 1 h, the reaction mixture was poured into 100 mL of ice water and the resulting precipitate was removed by filtration and washed with ice cold water. The resulting solid was dried to yield 2 as a pale yellow solid (4 g, 72%). The compound was used in the next step without further purification.

(S)-9,10-difluoro-3-methyl-8-nitro-7-oxo-3,7-dihydro-2H-(1,4)oxazino(2,3,4-ij)quinoline-6-carboxamide (3)

Compound 2 (4 g, 12.2 mmol) was suspended in $SOCl_2$ (25 mL) and refluxed for 2-3 h until a clear solution was obtained. Upon completion of the reaction, $SOCl_2$ was removed under vacuo. The remaining solid was diluted with dioxane and cooled in an ice bath. A solution of concentrated $NH_4OH$ was added carefully under vigorous stirring. A precipitate formed that was collected by filtration and washed with water. The solid was dried under vacuo to give amide 3 (3.3 g, 81% yield). This compound was used in the next step without further purification.

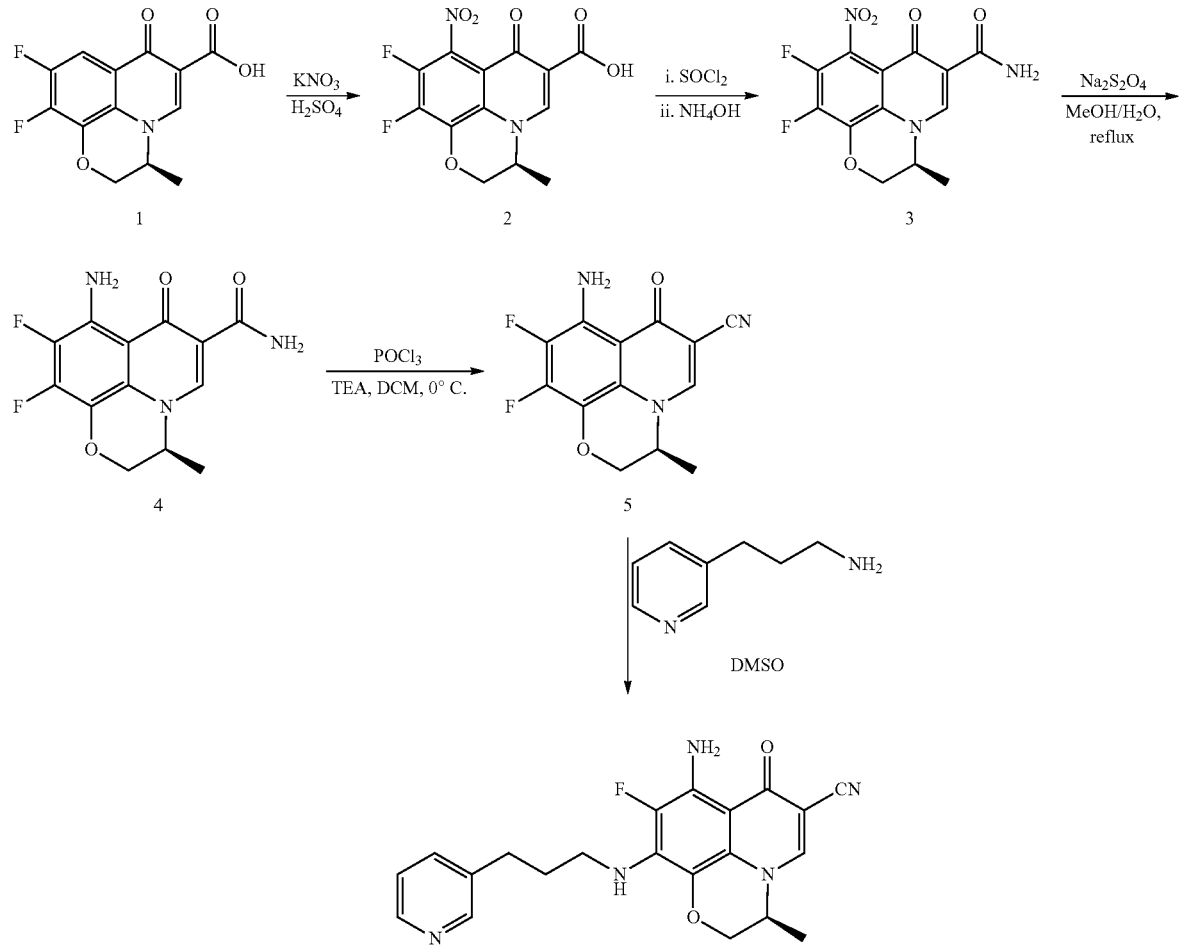

(S)-8-amino-9,10-difluoro-3-methyl-7-oxo-3,7-dihydro-2H-(1,4)oxazino(2,3,4-ij)quinoline-6-carboxamide (4)

To a suspension of 3 (1 g, 3.07 mmol) in a mixture of water/methanol (1:1 v/v, 30 mL) was added sodium hydrosulfite (Na$_2$S$_2$O$_4$, 4.3 g, 24.6 mmol). The suspension was refluxed for 5 h until all starting material has disappeared. Upon completion, the reaction mixture was cooled to room temperature and 50 mL of water were added. After 20 minutes, a light yellow solid was collected by filtration and washed with water. The solid was dried under vacuo to give 4 (725 mg, 74% yield), which was used in the next step without further purification.

(S)-8-amino-9,10-difluoro-3-methyl-7-oxo-3,7-dihydro-2H-(1,4)oxazino(2,3,4-ij)quinoline-6-carbonitrile (5)

To a solution of 4 (500 mg, 1.69 mmol) and triethylamine (1.2 mL, 8.5 mmol.) in DCM (20 mL) was added POCl$_3$ (431 µL, 3.2 mmol.) dropwise under Ar (or N$_2$) at 0° C. Stirring was continued for an additional 5 h. A dark colored mixture was formed. Upon completion of the reaction, DCM was removed under vacuo and the residue was washed several times with water. The solid was dried under vacuum to give 5 (385 mg, 82% yield). This product was not very soluble except in DMF or DMSO and was used in the next step without further purification.

Preparation of (S)-8-amino-9-fluoro-3-methyl-7-oxo-10-(3-(pyridin-3-yl)propylamino)-3,7-dihydro-2H-(1,4)oxazino(2,3,4-ij)quinoline-6-carbonitrile

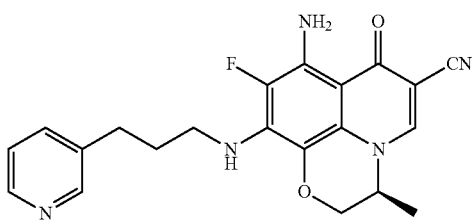 [SMILES: C[C@H]1COc2c(NCCCc3cccnc3)c(F)c(N)c3c(=O)c(C#N)cn1c23]

To a solution of 5 (30 mg, 0.108 mmol) in 5 ml of DMSO, 29.5 mg (0.216 mmol) of 3-(pyridine-3-yl)propan-1-amine were added. The reaction mixture was heated to 120° C. for 3 h. The DMSO was removed under vacuo and the remaining solid was purified by preparative HPLC to give the title compound as a yellow solid (6.4 mg, 15% yield).

MS (EP) m/z: 394.1 (M+1). (Calcd. for C$_{21}$H$_{20}$FN$_5$O$_2$, 393.16).

Example 2

Preparation of (S)-8-amino-9-fluoro-3-methyl-10-(3-(3-methylpyridin-2-yl)propylamino)-7-oxo-3,7-dihydro-2H-(1,4)oxazino(2,3,4-ij)quinoline-6-carbonitrile

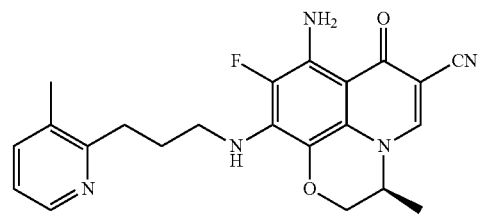 [SMILES: Cc1cccnc1CCCNc1c(F)c(N)c2c(=O)c(C#N)cn3c2c1OC[C@@H]3C]

This compound was prepared according to the synthetic procedures described above in Example 1 or routine modification thereof.

(39% yield) MS (EP) m/z: 408.1 (M+1). (Calcd. for C$_{22}$H$_{22}$FN$_5$O$_2$, 407.18).

Example 3

Preparation of 8-amino-9-fluoro-3,3-dimethyl-7-oxo-10-(3-(pyridin-2-yl)propylamino)-3,7-dihydro-2H-(1,4)oxazino(2,3,4-ij)quinoline-6-carbonitrile

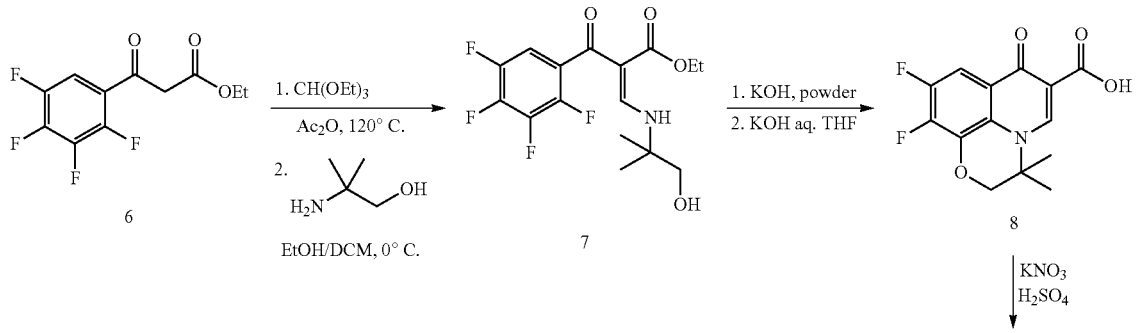

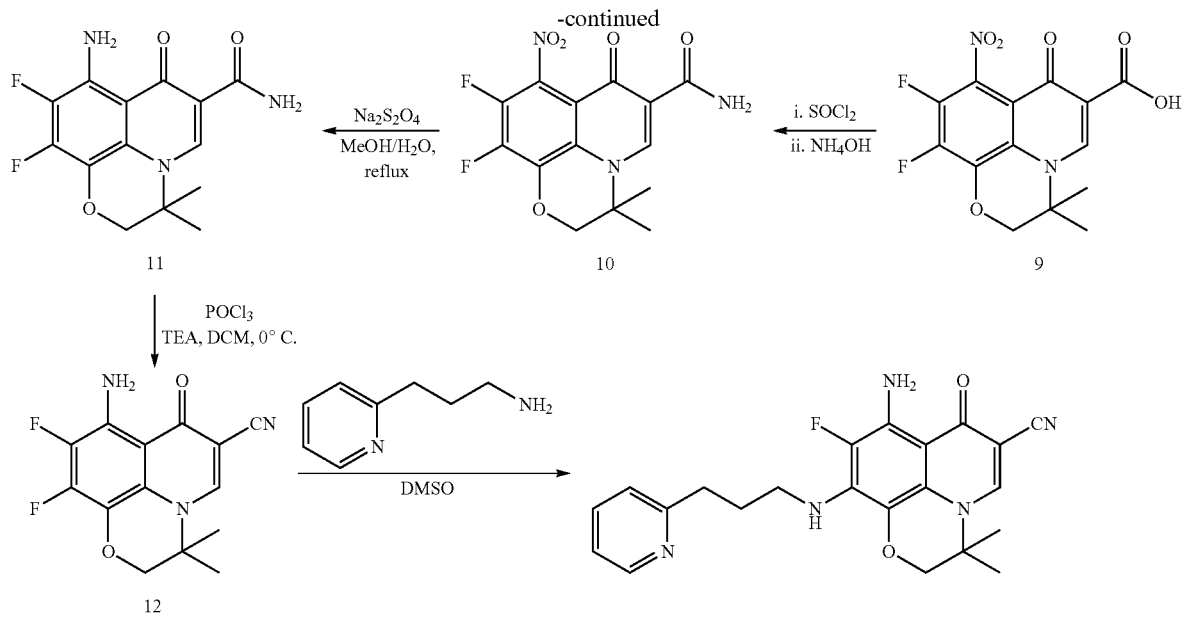

(Z)-ethyl 3-(1-hydroxy-2-methylpropan-2-ylamino)-2-(2,3,4,5-tetrafluorobenzoyl)acrylate (7)

A stirred solution of commercially available ethyl 3-oxo-3-(2,3,4,5-tetrafluorophenyl)propanoate (6) (15 g, 56.8 mmol), acetic anhydride (13.4 mL, 142 mmol) and triethyl orthoformate (14.1 mL, 18 mmol) was heated at 120° C. for 1.5 h. The mixture was concentrated in vacuo and dried under high vacuum for 5 hours. 10.1 g (31.5 mmol) of the crude product were dissolved in EtOH/DCM (30 mL) and cooled to 0° C. 2-Amino-2-methylpropan-1-ol (3.36 mL, 34.7 mmol) was added very slowly to this solution. After 30 minutes, the solvent was removed by evaporation and the product was freeze-dried to yield 7, as a yellow solid (11.9 g crude) that was used in the next step without further purification.

9,10-Difluoro-3,3-dimethyl-7-oxo-3,7-dihydro-2H-(1,4)oxazino(2,3,4-ij)quinoline-6-carboxylic acid (8)

To a solution of 7 (11.2 g, 30.8 mmol) in THF (45 mL), crushed pellets of KOH (4.32 g, 77 mmol) were added under ice-cooling. After 1.5 h, 50 mL of 10% aqueous KOH were added and the reaction mixture was heated up slowly to 85° C. and stirred for another 2 hours. The reaction mixture was acidified with 1 N HCl to pH 4. The white precipitate was collected by filtration to give 8, which was used without further purification in the next step (7.5 g, 83% yield).

9,10-difluoro-3,3-dimethyl-8-nitro-7-oxo-3,7-dihydro-2H-(1,4)oxazino(2,3,4-ij)quinoline-6-carboxylic acid (9)

A solution of 8 (7.5 g, 25.4 mmol) in concentrated $H_2SO_4$ (30 mL) was treated portionwise at 0° C. with solid $KNO_3$ (3.9 g, 38.6 mmol). After stirring at 0° C. for 2 h, the reaction mixture was poured into 500 mL of ice-water and the resulting precipitate was removed by filtration and washed with ice-cold water. The resulting solid was dried to yield 9 as a yellow solid (7.6 g, 87% yield).

9,10-difluoro-3,3-dimethyl-8-nitro-7-oxo-3,7-dihydro-2H-(1,4)oxazino(2,3,4-ij)quinoline-6-carboxamide (10)

A mixture of 9 (7.62 g, 22.4 mmol) and $SOCl_2$ (80 ml) was refluxed for 3 h until a clear solution was obtained. Upon completion, $SOCl_2$ was removed under vacuo. The remaining solid was taken up in 1,4-dioxane and the mixture was cooled to 0° C. A concentrated $NH_4OH$ solution (150 mL) was added slowly under vigorous stirring to the mixture, while the temperature was maintained at 0° C. A precipitate formed that was collected by filtration and washed with ice-cold water. The solid was dried to give compound 10 (6.85 g, 90% yield). This compound was used in the next step without further purification.

8-amino-9,10-difluoro-3,3-dimethyl-7-oxo-3,7-dihydro-2H-(1,4)oxazino(2,3,4-ij)quinoline-6-carboxamide (11)

To a suspension of 10 (6.3 g, 18.6 mmol) in a mixture of water/methanol 1/1 v/v (160 mL), sodium hydrosulfite (19.4 g, 116 mmol) was added and the suspension was refluxed for 5 h until all starting material was consumed. The product was collected by filtration while the mixture was still hot and washed with warm water. The solid was dried under vacuum to give 11 (2.92 g, 51% yield).

8-amino-9,10-difluoro-3,3-dimethyl-7-oxo-3,7-dihydro-2H-(1,4)oxazino(2,3,4-ij)quinoline-6-carbonitrile (12)

A mixture of 11 (2.92 g, 9.44 mmol) and triethylamine (6.6 mL, 47 mmol) in $CH_2Cl_2$ (20 ml) was cooled to 0° C. and $POCl_3$ (4.35 g, 28 mmol) was added drop wise with stirring. The mixture was stirred an additional 5 h at 0° C. During that time, the reaction mixture turned dark-brown. Upon completion of the reaction, the solvent was removed by evaporation. 70 mL of water were added and the mixture stirred at room temperature for 1 h. The precipitate that formed was collected by filtration and washed with water. The solid was dried under vacuum to yield 12 as a brown solid (2.6 g, 94%). This compound was used without further purification in the next step.

8-amino-9-fluoro-3,3-dimethyl-7-oxo-10-(3-(pyridin-2-yl)propylamino)-3,7-dihydro-2H-(1,4)oxazino(2,3,4-ij)quinoline-6-carbonitrile

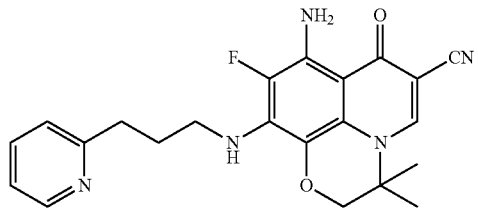 [SMILES: CC1(C)COc2c(NCCCc3ccccn3)c(F)c(N)c3c(=O)c(C#N)cn1c23]

To a solution of 12 (250 mg, 0.86 mmol) in 4 ml of DMSO, 268 mg (1.98 mmol) of 3-(pyridin-2-yl)propan-1-amine were added. The reaction mixture was heated to 120° C. for 5 h. After cooling, the reaction mixture was freeze dried to remove DMSO and the remaining solid was purified by preparative HPLC to give the title compound as a yellow solid (102 mg, 29% yield).

MS (EP) m/z: 408.1 (M+1). (Calcd. for $C_{22}H_{22}FN_5O_2$, 407.18).

Example 4

Preparation of 8-amino-9-fluoro-3,3-dimethyl-10-(3-(3-methylpyridin-2-yl)propylamino)-7-oxo-3,7-dihydro-2H-(1,4)oxazino(2,3,4-ij)quinoline-6-carbonitrile

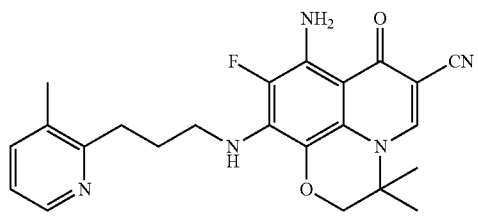 [SMILES: Cc1cccnc1CCCNc1c(F)c(N)c2c(=O)c(C#N)cn3c2c1OCC3(C)C]

This compound was prepared according to the synthetic procedures described above in Example 3 or routine modification thereof.

(23% yield) MS (EP) m/z: 422.1 (M+1). (Calcd. for $C_{23}H_{24}FN_5O_2$, 421.19).

Example 5

Preparation of 8-amino-9-fluoro-3,3-dimethyl-7-oxo-10-(3-(pyridin-3-yl)propylamino)-3,7-dihydro-2H-(1,4)oxazino(2,3,4-ij)quinoline-6-carbonitrile

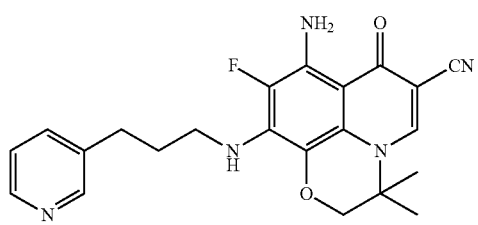 [SMILES: CC1(C)COc2c(NCCCc3cccnc3)c(F)c(N)c3c(=O)c(C#N)cn1c23]

This compound was prepared according to the synthetic procedures described above in Example 3 or routine modification thereof.

(27% yield) MS (EP) m/z: 408.1 (M+1). (Calcd. for $C_{22}H_{22}FN_5O_2$, 407.18).

Example 6

Preparation of (S)-10-(3-(1H-imidazol-1-yl)propylamino)-8-amino-9-fluoro-3-methyl-6-(1H-tetrazol-5-yl)-2H-(1,4)oxazino(2,3,4-ij)quinolin-7(3H)-one

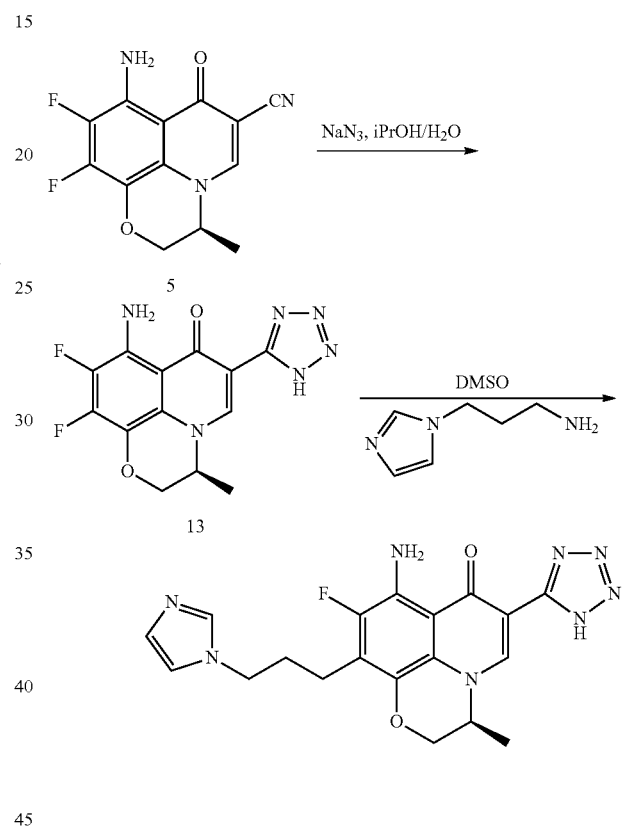

Preparation of (S)-8-amino-9,10-difluoro-3-methyl-6-(1H-tetrazole-5-yl)-2H-(1,4)oxazino(2,3,4-ij)quinolin-7(3H)-one (13)

To a mixture of nitrile 5 (40 mg, 0.14 mmol) in isopropanol and water (1:1 v/v, 15 ml) were added 20 mg of sodium azide (0.29 mmole) and 22 mg of zinc chloride (0.29 mmole). The mixture was heated to 110° C. for 18 h. The precipitates were collected by filtration and washed with water. The solid was dried under vacuum to give 27 mg (60% yield) of 13. This title compound was used without further purification in the next step.

Preparation of (S)-10-(3-(1H-imidazol-1-yl)propylamino)-8-amino-9-fluoro-3-methyl-6-(1H-tetrazol-5-yl)-2H-(1,4)oxazino(2,3,4-ij)quinolin-7(3H)-one To a solution of 13 (250 mg, 0.78 mmol) in 5 ml of DMSO were added 132 μl (1.17 mmol) of 3-(1H-imidazol-1-yl)propan-1-amine. The reaction mixture was heated to 120° C. for 1 h. Upon completion of the reaction the DMSO was removed and the remaining solid was purified by preparative HPLC. To the combined HPLC fractions containing the product were added several drops of 1 N HCl before they were dried down to generate the HCl salt of the compound. The title compound was obtained as a yellow solid (118 mg, 37% yield).

MS (EP) m/z: 426.4 (M+1). (Calcd. for $C_{19}H_{20}FN_9O_2$, 425.42)

The following compounds were prepared using synthetic procedures similar to those described above or routine modifications thereof.

Example 7

Preparation of (S)-8-amino-10-(3-(ethyl(phenyl)amino)propylamino)-9-fluoro-3-methyl-6-(1H-tetrazol-5-yl)-2H-(1,4)oxazino(2,3,4-ij)quinolin-7(3H)-one

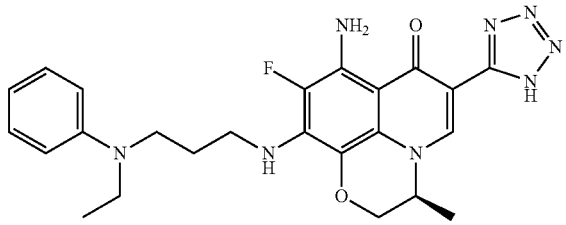 [SMILES: CCN(CCCNc1c(F)c(N)c2c(=O)c(-c3nnn[nH]3)cn3c2c1OC[C@@H]3C)c1ccccc1]

MS (EP) m/z: 479.5 (M+1). (Calcd. for $C_{24}H_{27}FN_8O_2$, 478.52).

Example 8

Preparation of (S)-8-amino-9-fluoro-3-methyl-10-(3-(pyridin-2-yl)propylamino)-6-(1H-tetrazol-5-yl)-2H-(1,4)oxazino(2,3,4-ij)quinolin-7(3H)-one

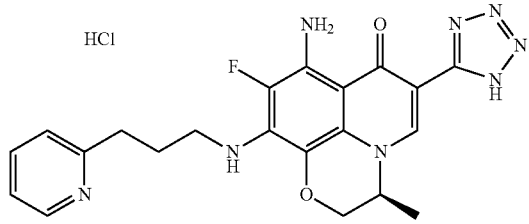 [SMILES: C[C@H]1COc2c(NCCCc3ccccn3)c(F)c(N)c3c(=O)c(-c4nnn[nH]4)cn1c23 ; Cl]

MS (EP) m/z: 437.4 (M+1). (Calcd. for $C_{21}H_{21}FN_8O_2$, 436.44) m, 1H), 6.96-6.94 (m, 2H), 6.46 (bs, 2H), 6.10 (s, 1H), 4.01 (s, 2H), 1.56 (s, 6H)

Example 9

Glycogen Synthesis Activity in Hep G2 Cells

Hep G2 cells were obtained from the Japanese Collection of Research Bioresources and were grown in standard culture medium, a low-glucose Dulbecco's modified Eagle's medium (DMEM) containing 10% fetal calf serum supplemented with 100 U/mL penicillin and 100 µg/mL streptomycin, in a humidified and 5% $CO_2$ atmosphere kept at 37° C. The Hep G2 cells were harvested with 0.25% trypsin solution containing 1 mM EDTA, and were seeded on 12 well plates at $1\times10^5$ cells per well. Following a culture for 3 days, the cells were washed once with phosphate buffered saline (PBS), and were incubated with serum-free low-glucose DMEM supplemented with 100 U/mL penicillin and 100 µg/mL streptomycin. Following a culture for 3 hrs, compounds provided herein at various concentrations and 2.5 µCi/mL D-(2-$^3$H)glucose (PerkinElmer, Boston, Mass., USA) were added to the serum-free low-glucose DMEM. A vehicle control of DMSO (0.3%, final concentration) was also used. The total volume per well of the reaction medium was 1.0 mL of serum-free low-glucose DMEM. After incubation at 37° C. for 3 hrs, the medium was aspirated and cells were washed twice with PBS, and 0.25 mL of 1 N KOH containing 0.4 mg/mL carrier glycogen were added. After incubation at 37° C. for 30 min, 0.25 mL of 48.8% (w/v) KOH was added to each well for cell lysis. After incubation at 95° C. for 30 min, 1.5 mL of 95% (v/v) ethanol was added to the cell lysate. Total glycogen was precipitated overnight at −20° C. Glycogen precipitates were recovered by centrifugation at 19,000×g for 30 min at 4° C. Precipitates were washed once with 1 mL of 70% (v/v) ethanol, and were re-suspended in 0.5 mL water. ($^3$H)Glucose incorporation into glycogen was assessed using a liquid scintillation counter (Packard Instrument Co., Meriden, Conn., USA).

Example 10

Animal Study (Oral Glucose Tolerance Test)

Male Crlj:CD1 (ICR) mice were obtained from Charles River Laboratries Japan (Yokohama, Japan). All mice were given a standard diet (Clea Japan, Tokyo, Japan) and tap water ad libitum. All institutional guidelines for animal care and use were applied in this study. Test compounds were suspended in 0.3% carboxymethyl-cellulose sodium salt (CMC-Na; Sigma, St. Louis, Mo.). After fasting for 15-17 hr, the test compound (30 mg/kg) or vehicle (0.3% CMC-Na) was orally administered to 7-week-old ICR mice. Glucose solution (5 g/kg) was orally administered at 30 min after test compound treatment. Blood samples were collected from tail vein using capillary tubes containing EDTA•2K before test compound treatment, and at 0, 0.5, 1, and 2 hr after glucose load. The blood samples were centrifuged at 2,500×g for 5 min and separated plasma was kept on ice and analyzed in the same day. Plasma glucose levels were determined using the glucose C II-test (Wako Pure Chemical Industries, Osaka, Japan).

Repeat Dose Study

Male ob/ob or C57BL/6J mice were obtained from Charles River Laboratories Japan (Yokohama, Japan). All mice were given OA-2 diet (Japan Clea, Tokyo, Japan) and tap water ad libitum. All institutional guidelines for animal care and use were applied in this study. Each test compound was suspended in 0.3% carboxymethyl-cellulose sodium salt (0.3% CMC-Na; Sigma, St. Louis, Mo.). Ten mg/kg of test compound was orally administrated once a day for 14 days to 6-week-old ob/ob or C57BL/6J mice. Blood samples were collected from the tail vein using capillary tubes containing EDTA2K at 12 hour after administration for 7 and 14 days. The blood samples were centrifuged at 2,500×g for 5 min and separated plasma was kept on ice and analyzed the same day. Plasma glucose levels were determined using the Glucose C II-test (Wako Pure Chemical Industries, Osaka, Japan).

The following compound was tested in this assay:

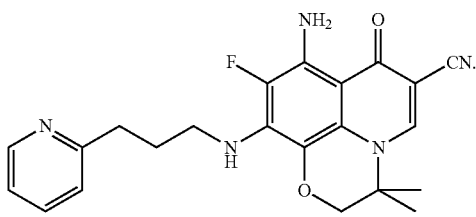 [SMILES: CC1(C)COc2c(NCCCc3ccccn3)c(F)c(N)c3c(=O)c(C#N)cn1c23]

In certain embodiments, the compounds provided herein lowered glucose from about 15-70%.

Dog Emesis Study

Male beagle dogs were obtained from Japan Laboratory Animals Inc. (Tokyo, Japan). The dogs were fed on a standard diet (Oriental Yeast, Tokyo, Japan). Water was available ad libitum. Test compounds were dissolved in dimethyl sulfoxide (100 mg/mL) followed by a dilution with 50% polyethylene glycol 400 to give a concentration of 1, 3 and 10 mg/mL. The dogs were dosed intravenously via cephalic vein with the compounds (0.1, 0.3 and 1 mg/kg, 0.1 mL/kg). Blood samples were collected from opposite cephalic vein into evacuated tube containing EDTA-2K (VENOJECT II, Terumo, Tokyo, Japan) at 0.17, 0.5, 1, 2, and 4 h postdose and kept on ice. Plasma samples were separated by centrifugation (2200×g, 10 min, 4° C.) and stored at −20° C. The plasma samples were mixed with 2 volume of the mixture of methanol and acetonitrile (1:1, v/v) containing internal standard and centrifuged at 13400×g for 3 min. The supernatant was diluted 20 times with 15% acetonitrile and a 10-μL aliquot was subjected into LC/MS/MS system. Separation by HPLC was conducted with a Waters Alliance 2795 Separations Module (Waters Corp., MA). Mass spectra were determined using a Micromass Quattro Ultima Pt (Waters Corp.) with an electrospray ionization interface in the MRM mode using positive ion pairs.

The following compounds were tested in this study:

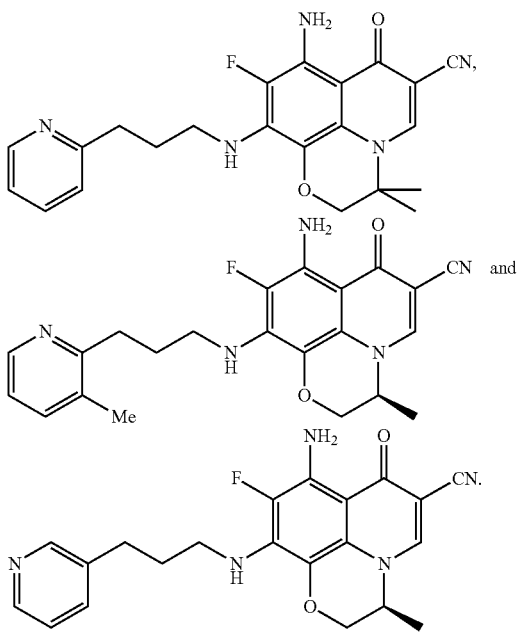

In certain embodiments, the test compounds showed $T_{1/2}$ in the range of 0.5 to 12 h. In certain embodiments, the test compounds showed $C_{10min}$ in the range 1-5 μm. In certain embodiments, emesis was examined in dogs treated with test compounds.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound of Formula I:

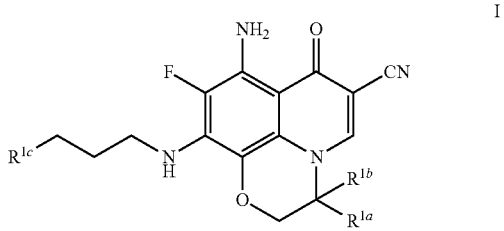

or a pharmaceutically acceptable derivative thereof, wherein $R^{1a}$ and $R^{1b}$ are each independently hydrogen or lower alkyl, and $R^{1c}$ is a substituted or unsubstituted pyridinyl; wherein the substituents when present are selected from one or more lower alkyl groups, with a proviso that when a) one of $R^{1a}$ and $R^{1b}$ is hydrogen and the other is methyl and b) $R^{1c}$ is pyridin-2-yl, then $R^{1c}$ is substituted with one or more lower alkyl groups.

2. The compound of claim 1, wherein $R^{1a}$ and $R^{1b}$ are each lower alkyl.

3. The compound of claim 1, wherein $R^{1a}$ and $R^{1b}$ are each methyl.

4. The compound of claim 1, wherein $R^{1a}$ is hydrogen and $R^{1b}$ is lower alkyl.

5. The compound of claim 1, wherein $R^{1a}$ is hydrogen and $R^{1b}$ is methyl.

6. The compound of claim 1, wherein $R^{1c}$ is substituted with one or two methyl groups.

7. The compound of claim 1, wherein the compound has Formula:

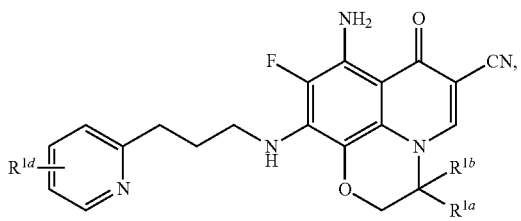

or a pharmaceutically acceptable derivative thereof, wherein $R^{1d}$ is hydrogen or lower alkyl.

8. The compound of claim 7, wherein $R^{1d}$ is hydrogen or methyl.

9. The compound of claim 7, wherein $R^{1d}$ is hydrogen.

10. The compound of claim 7, wherein $R^{1d}$ is methyl.

11. The compound of claim 1, wherein the compound has Formula:

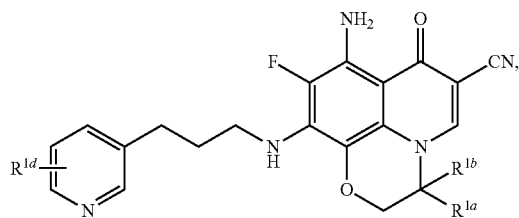

or a pharmaceutically acceptable derivative thereof, wherein $R^{1d}$ is hydrogen or lower alkyl.

12. The compound of claim 1, wherein the compound has Formula:

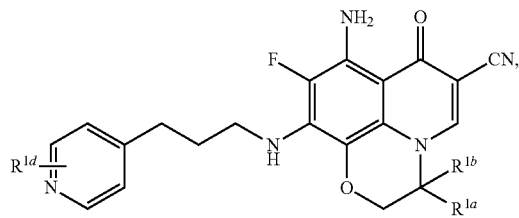

or a pharmaceutically acceptable derivative thereof, wherein $R^{1d}$ is hydrogen or lower alkyl.

13. The compound of claim 1, wherein the compound has Formula:

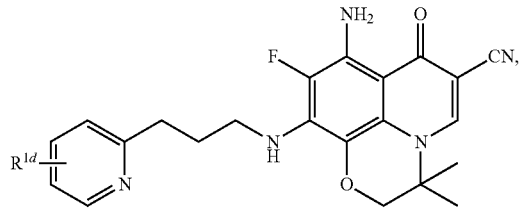

or a pharmaceutically acceptable derivative thereof, wherein $R^{1d}$ is hydrogen or lower alkyl.

14. The compound of claim 11, wherein the compound has Formula:

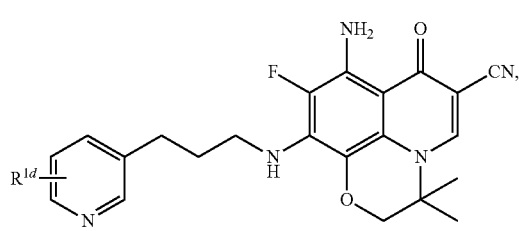

or a pharmaceutically acceptable derivative thereof, wherein $R^{1d}$ is hydrogen or lower alkyl.

15. The compound of claim 13, wherein the compound has Formula:

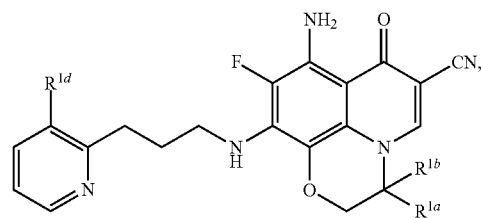

or a pharmaceutically acceptable derivative thereof.

16. The compound of claim 12, wherein the compound has Formula:

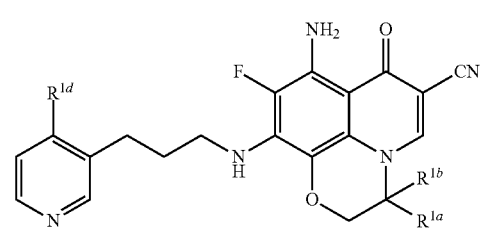

or a pharmaceutically acceptable derivative thereof.

17. The compound of claim 1, wherein the compound has Formula:

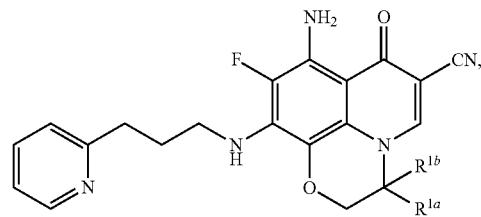

or a pharmaceutically acceptable derivative thereof.

18. The compound of claim 1, wherein the compound has Formula:

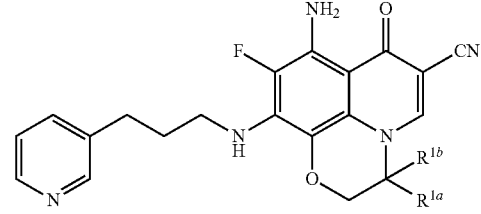

or a pharmaceutically acceptable derivative thereof.

19. The compound of claim 1, wherein the compound has Formula:

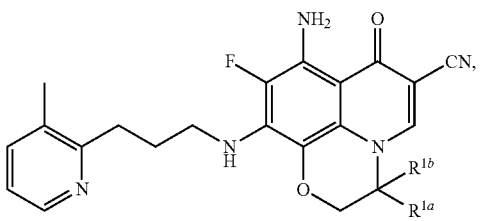

or a pharmaceutically acceptable derivative thereof.

20. The compound of claim 1, wherein the compound has Formula:

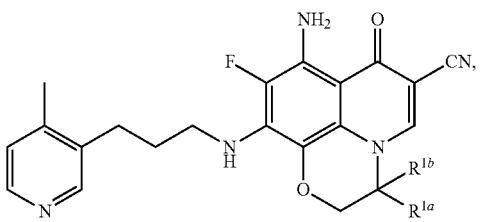

or a pharmaceutically acceptable derivative thereof.

21. The compound of claim 1 selected from:

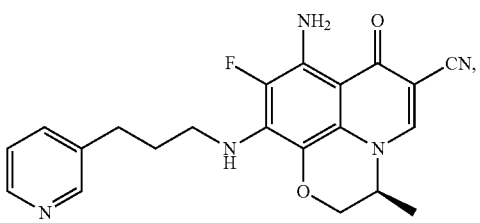

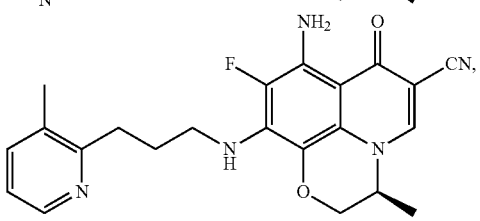

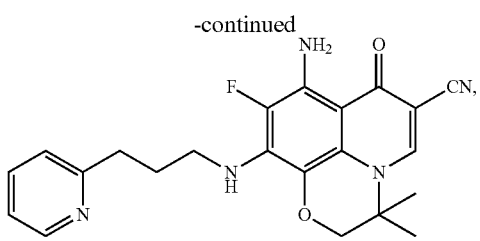

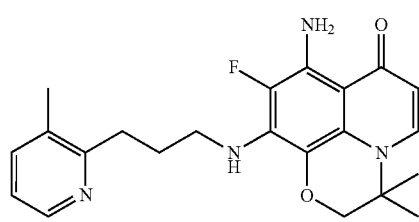

and

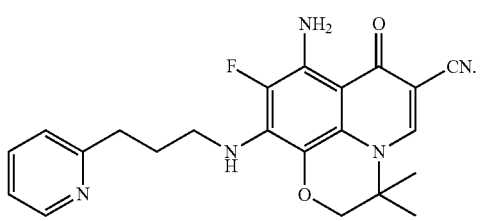

22. A pharmaceutical composition comprising a compound of claim 1 and a pharmaceutically acceptable carrier.

23. A method for treating or ameliorating a GSK-3 mediated disease selected from Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases, depression, bipolar mood disorders, rheumatoid arthritis, inflammatory bowel disease, ulceractive colitis, Crohn's disease, sepsis, pancreatic cancer, ovarian cancer and osteoporosis.

\* \* \* \* \*

UNITED STATES PATENT AND TRADEMARK OFFICE
CERTIFICATE OF CORRECTION

PATENT NO. : 8,389,514 B2
APPLICATION NO. : 12/677789
DATED : March 5, 2013
INVENTOR(S) : Li et al.

It is certified that error appears in the above-identified patent and that said Letters Patent is hereby corrected as shown below:

In the Claims

In Claim 21, Col. 50, line 25-30, replace " 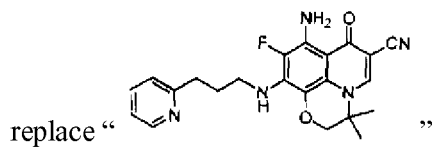 "

with -- 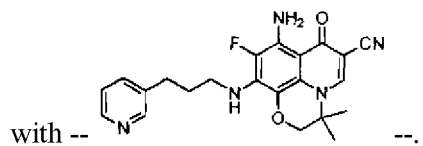 --.

Signed and Sealed this
Second Day of July, 2013

Teresa Stanek Rea
*Acting Director of the United States Patent and Trademark Office*